US012150842B2

(12) United States Patent
Schoon et al.

(10) Patent No.: US 12,150,842 B2
(45) Date of Patent: Nov. 26, 2024

(54) ELASTICATED MATERIAL WITH NON-CONTINUOUS CHANNELS

(71) Applicant: Kimberly-Clark Worldwide, Inc., Neenah, WI (US)

(72) Inventors: Bradley W. Schoon, Oshkosh, WI (US); Chadwick I. Romzek, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 138 days.

(21) Appl. No.: 16/608,565

(22) PCT Filed: Apr. 27, 2018

(86) PCT No.: PCT/US2018/029751
§ 371 (c)(1),
(2) Date: Oct. 25, 2019

(87) PCT Pub. No.: WO2018/200933
PCT Pub. Date: Nov. 1, 2018

(65) Prior Publication Data
US 2020/0179183 A1    Jun. 11, 2020

Related U.S. Application Data

(60) Provisional application No. 62/491,503, filed on Apr. 28, 2017.

(51) Int. Cl.
*A61F 13/49*  (2006.01)
*A61F 13/495* (2006.01)
(Continued)

(52) U.S. Cl.
CPC .... *A61F 13/49012* (2013.01); *A61F 13/4902* (2013.01); *A61F 13/495* (2013.01);
(Continued)

(58) Field of Classification Search
CPC ............ A61F 13/49012; A61F 13/4902; A61F 13/495; A61F 13/539; A61F 2013/49025;
(Continued)

(56) References Cited

U.S. PATENT DOCUMENTS 6,291,039 B1    9/2001  Combe et al.
7,297,139 B2    11/2007 Price et al.
(Continued)

FOREIGN PATENT DOCUMENTS

CN    1582224 A    2/2005
EP    3563817 A1   11/2019
(Continued)

*Primary Examiner* — Vincent Tatesure
(74) *Attorney, Agent, or Firm* — KIMBERLY-CLARK WORLDWIDE, INC.

(57) ABSTRACT

Elasticated materials and methods of forming elasticated materials are disclosed. In one embodiment, an elasticated material may comprise a first layer of material, a second layer of material bonded to the first layer of material by a plurality of bonds arranged in bond groupings aligned in bond grouping rows, and an elastomeric strand extending in the lateral direction and disposed between the first layer and the second layer, the elastomeric strand extending between a first bond and a second bond of a first bond grouping with the first bond and the second bond of the first bond grouping being spaced apart in the longitudinal direction a distance less than an un-tensioned diameter of the elastomeric strand. A portion of a second bond grouping may laterally overlap the first bond grouping with the second bond grouping disposed row that is longitudinally adjacent to the row containing the first bond grouping.

13 Claims, 3 Drawing Sheets

(51) Int. Cl.
*A61F 13/539* (2006.01)
*B32B 5/02* (2006.01)
*B32B 3/08* (2006.01)
*B32B 7/05* (2019.01)

(52) U.S. Cl.
CPC ............ *A61F 13/539* (2013.01); *B32B 5/022* (2013.01); *A61F 2013/49025* (2013.01); *B32B 3/085* (2013.01); *B32B 5/026* (2013.01); *B32B 7/05* (2019.01); *B32B 2555/02* (2013.01); *Y10T 428/24826* (2015.01); *Y10T 442/69* (2015.04)

(58) Field of Classification Search
CPC ......... B32B 3/085; B32B 5/022; B32B 5/026; B32B 7/05; Y10T 428/24826; Y10T 442/69
USPC ......................................................... 442/327
See application file for complete search history.

(56) References Cited

U.S. PATENT DOCUMENTS

| | | | |
|---|---|---|---|
| 7,582,348 | B2 | 9/2009 | Ando et al. |
| 8,647,319 | B2 * | 2/2014 | Een ................ A61F 13/49011 604/385.27 |
| 9,011,404 | B2 | 4/2015 | Kobayashi et al. |
| 2001/0025683 | A1 | 10/2001 | Burriss et al. |
| 2002/0166617 | A1 | 11/2002 | Molander et al. |
| 2003/0111157 | A1 | 6/2003 | Ehlert et al. |
| 2003/0144643 | A1 | 7/2003 | Jarpenberg et al. |
| 2006/0144904 | A1 | 7/2006 | Mlinar et al. |
| 2007/0172628 | A1 | 7/2007 | Seth et al. |
| 2010/0076394 | A1 | 3/2010 | Hayase et al. |
| 2012/0095429 | A1 * | 4/2012 | Kobayashi ........ A61F 13/15804 604/385.16 |
| 2014/0034213 | A1 | 2/2014 | Cham et al. |
| 2014/0088535 | A1 | 3/2014 | Xu et al. |
| 2014/0248471 | A1 | 9/2014 | Hanschen et al. |
| 2015/0144270 | A1 | 5/2015 | Nakakado |
| 2015/0267327 | A1 | 9/2015 | Kanya |
| 2016/0024617 | A1 | 1/2016 | Auxier, II et al. |
| 2016/0058624 | A1 | 3/2016 | Hohm et al. |
| 2016/0106601 | A1 | 4/2016 | Kobayashi et al. |
| 2016/0159062 | A1 | 6/2016 | Sablone |
| 2016/0228305 | A1 | 8/2016 | Gualtieri et al. |
| 2016/0288407 | A1 | 10/2016 | Ehlert et al. |
| 2016/0331600 | A1 | 11/2016 | Polidori et al. |

FOREIGN PATENT DOCUMENTS

| | | |
|---|---|---|
| EP | 3572053 A1 | 11/2019 |
| EP | 3692960 A1 | 8/2020 |
| EP | 3703948 A2 | 9/2020 |
| WO | 9855292 A1 | 12/1998 |
| WO | 0149905 A2 | 7/2001 |
| WO | 06038939 A1 | 4/2006 |
| WO | 16160752 A1 | 10/2016 |
| WO | 2018122970 A1 | 7/2018 |
| WO | 2018154685 A1 | 8/2018 |

* cited by examiner

ELASTICATED MATERIAL WITH NON-CONTINUOUS CHANNELS

CROSS-REFERENCE TO RELATED APPLICATION

This application claims the benefit of U.S. Provisional Application No. "62/491,503", titled "ELASTICATED MATERIAL WITH NON-CONTINUOUS CHANNELS", and filed Apr. 28, 2017.

TECHNICAL FIELD

The present disclosure relates to elasticated materials, and more specifically elasticated materials that have non-continuous channels.

BACKGROUND OF THE DISCLOSURE

Elasticated materials are used in many different applications, including within various clothing garments and absorbent articles. Such elasticated materials may be used as part of waistbands, leg cuffs, barrier cuffs, or in other components of clothing garments and absorbent articles to provide beneficial fit characteristics, help prevent leakage of bodily exudates, or impart other benefits.

Many present clothing garments and absorbent articles include elasticated materials which comprise elastic strands positioned between layers of material and affixed to the layers of material with adhesive. Some prior art elasticated materials have attempted to remove the adhesive in favor of affixing the elastic strands to the layers of material with the use of discrete individual bonds. These prior art materials position the bonds across the elastic strands a distance less than the un-tensioned diameter of the elastic strands. Some example prior art materials can be seen in U.S. Pat. No. 6,291,039 to Cera France Compagnie d'Equipment Robotique Appliquee, titled "Ruffling Slide and Method for Making Same". This particular structural configuration holds the elastic strands in place within the elasticated material between the bonds. These adhesive-less elasticated materials have a cost advantage as they do not require adhesive to affix the elastomeric strands within the elasticated material. Accordingly, additional elasticated materials which do not include adhesive may be desired to help reduce overall costs of absorbent articles, in addition to having functional benefits.

SUMMARY OF THE DISCLOSURE

The present disclosure relates to elasticated materials, and more specifically elasticated materials that have non-continuous channels. In general, the elasticated materials of the present disclosure are constructed so that the channels formed in the elasticated material when the material is in a relaxed state do not extend continuously through the material. For instance, the relaxed material may have a number of ridges and a number of valleys—or channels. The materials of the present disclosure are constructed so that the channels do not align to provide a continuous path through the material. Such materials can be used in absorbent articles or clothing garments in order to help prevent leakage of the articles or garments.

In a first embodiment, an elasticated material may extend in a longitudinal direction and a lateral direction, and the material may comprise a first layer of material, a second layer of material bonded to the first layer of material by a plurality of bonds, the plurality of bonds being arranged in bond groupings aligned in bond grouping rows, and an elastomeric strand extending in the lateral direction and disposed between the first layer of material and the second layer of material, the elastomeric strand extending between a first bond and a second bond of a first bond grouping with the first bond and the second bond of the first bond grouping being spaced apart in the longitudinal direction a distance less than an un-tensioned diameter of the elastomeric strand. Additionally, a portion of a second bond grouping may laterally overlap the first bond grouping, the second bond grouping disposed in a bond grouping row longitudinally adjacent to the bond grouping row containing the first bond grouping.

In a second embodiment, each of the first bond grouping and the second bond grouping of the first embodiment may comprise a longitudinally superior bond and a longitudinally inferior bond, and the longitudinally inferior bond of the first bond grouping may laterally overlap the longitudinally superior bond of the second bond grouping.

In a third embodiment, the lateral overlap between the longitudinally inferior bond of the first bond grouping and the longitudinally superior bond of the second bond grouping of the second embodiment may comprise an overlap distance that is between 0% and 250% of a longitudinal height of the longitudinally inferior bond of the first bond grouping.

In a fourth embodiment, the lateral overlap between the longitudinally inferior bond of the first bond grouping and the longitudinally superior bond of the second bond grouping of any of the second or third embodiments may comprise an overlap distance that is between 0% and 100% of a longitudinal height of the longitudinally inferior bond of the first bond grouping.

In a fifth embodiment, the first bond grouping and the second bond grouping of any of the second through fourth embodiments may each comprise two bonds.

In a sixth embodiment, the first bond grouping and the second bond grouping of any of the second through further embodiments may each comprise three bonds.

In a seventh embodiment, the first bond grouping of any of the first through sixth embodiments may be spaced a first lateral distance from an adjacent bond grouping in the first bond grouping row, and the second bond grouping may be spaced a second lateral from the first bond grouping, the second lateral distance being between about 10% and about 40% of the first lateral distance.

In an eighth embodiment, the first bond grouping of any of the first through sixth embodiments may be spaced a first lateral distance from an adjacent bond grouping in the first bond grouping row, and the second bond grouping may be spaced a second lateral from the first bond grouping, the second lateral distance being between about 15% and about 30% of the first lateral distance.

In a ninth embodiment, each pair of adjacent bonds within a bond grouping of any of the first through eighth embodiments may be spaced apart longitudinally a distance less than an un-tensioned diameter of the elastomeric strand.

In a tenth embodiment, adjacent bond groupings within a bond grouping row of any of the first through ninth embodiments may be spaced apart a bond grouping lateral distance, and the smallest bond grouping lateral distance of a given bond grouping row may be less than the largest bond grouping lateral distance of the given bond grouping row by an amount less than or equal to 15% of the largest bond grouping lateral distance, for each bond grouping row of the elasticated material.

In an eleventh embodiment, an absorbent article including front region, a crotch region, and a rear region, the article having a first side edge and a second side edge may comprise a first elasticated waist panel disposed in the front region, a second elasticated waist panel disposed in the rear region and spaced from the first elasticated waist panel, and an absorbent panel comprising an outer cover, a liner, and an absorbent body disposed between the outer cover and the liner, the absorbent panel spanning between and connecting the first elasticated waist panel and the second elasticated waist panel. Further, one of the first elasticated waist panel and the second elasticated waist panel may comprise a first layer of material, a second layer of material bonded to the first layer of material by a plurality of bonds, the plurality of bonds being arranged in bond groupings aligned in bond grouping rows, and an elastomeric strand extending in the lateral direction and disposed between the first layer of material and the second layer of material, the elastomeric strand extending between a first bond and a second bond of a first bond grouping with the first bond and the second bond of the first bond grouping being spaced apart in the longitudinal direction a distance less than an un-tensioned diameter of the elastomeric strand. In some of these embodiments, a portion of a second bond grouping may laterally overlap the first bond grouping, the second bond grouping disposed in a bond grouping row longitudinally adjacent to the bond grouping row containing the first bond grouping.

In a twelfth embodiment, the elastomeric strand of the eleventh embodiment may overlap the absorbent body.

In a thirteenth embodiment, other one of the first elasticated waist panel and the second elasticated waist panel of any of the eleventh or twelfth embodiments may comprise a first layer of material, a second layer of material bonded to the first layer of material by a plurality of bonds, the plurality of bonds being arranged in bond groupings aligned in bond grouping rows, and an elastomeric strand extending in the lateral direction and disposed between the first layer of material and the second layer of material, the elastomeric strand extending between a first bond and a second bond of a first bond grouping with the first bond and the second bond of the first bond grouping being spaced apart in the longitudinal direction a distance less than an un-tensioned diameter of the elastomeric strand. In some of these embodiments, a portion of a second bond grouping may laterally overlap the first bond grouping, the second bond grouping disposed in a bond grouping row longitudinally adjacent to the bond grouping row containing the first bond grouping.

In a fourteenth embodiment, each of the first bond grouping and the second bond grouping of any of the eleventh through thirteenth embodiments may comprise a longitudinally superior bond and a longitudinally inferior bond, and the longitudinally inferior bond of the first bond grouping may laterally overlap the longitudinally superior bond of the second bond grouping.

In a fifteenth embodiment, the lateral overlap between the longitudinally inferior bond of the first bond grouping and the longitudinally superior bond of the second bond grouping of the fourteenth embodiment may comprise an overlap distance that is between 0% and 250% of a longitudinal height of the longitudinally inferior bond of the first bond grouping.

In a sixteenth embodiment, the lateral overlap between the longitudinally inferior bond of the first bond grouping and the longitudinally superior bond of the second bond grouping of the fourteenth embodiment may comprise an overlap distance that is between 0% and 100% of a longitudinal height of the longitudinally inferior bond of the first bond grouping.

In a seventeenth embodiment, the first bond grouping and the second bond grouping of any of the eleventh through sixteenth embodiments may each comprise two bonds.

In an eighteenth embodiment, the first bond grouping and the second bond grouping of any of the eleventh through sixteenth embodiments may each comprise three bonds.

In a nineteenth embodiment, each pair of adjacent bonds within a bond grouping of any of the eleventh through eighteenth embodiments may be spaced apart longitudinally a distance less than an un-tensioned diameter of the elastomeric strand.

In a twentieth embodiment, the first waist panel of any of the eleventh through nineteenth embodiments may comprise a plurality of elastomeric strands, each of the plurality of elastomeric strands extending through bonds of different bond groupings, the bonds of the different bond groupings spaced apart longitudinally a distance less than an un-tensioned diameter of the elastomeric strand passing therethrough.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The present disclosure relates to elasticated materials comprising bond patterns with beneficial properties. In some embodiments according the present disclosure, the bond pattern used to form an elasticated material allows for any positioning of the elastomeric strands in the forming process while ensuring bonding of the strands within the material. In further embodiments, the bond pattern used may cause an uneven ruffling of the elasticated material when the material is in a relaxed state. The uneven ruffling may have one or more benefits including being a barrier to fluid flow and also providing a relatively flat material in comparison to alternative bond patterns which form distinct, continuous ridges and valleys when the material is in a relaxed state.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, adult diapers and pants, medical garments, surgical pads and bandages, other personal care or health care garments, and the like without departing from the scope of the present disclosure.

The term "bonded", "attached" or "coupled" refers herein to the joining, adhering, connecting, attaching, or the like, of two elements. Two elements will be considered bonded, attached or coupled together when they are joined, adhered, connected, attached, or the like, directly to one another or indirectly to one another, such as when each is directly bonded to intermediate elements. The bonding, attaching or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer liquids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, hydroentangling processes, etc.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40.

Spunbond fibers are generally not tacky when they are deposited on a collecting surface.

The term "elasticated" when used herein to describe a material or a portion of an article means that the material or article is made of an inelastic sheet material coupled to elastomeric material, e.g. one or more elastomeric bands or strands, such that the material or article exhibits elastic properties.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Elasticated Material

Figure 1:
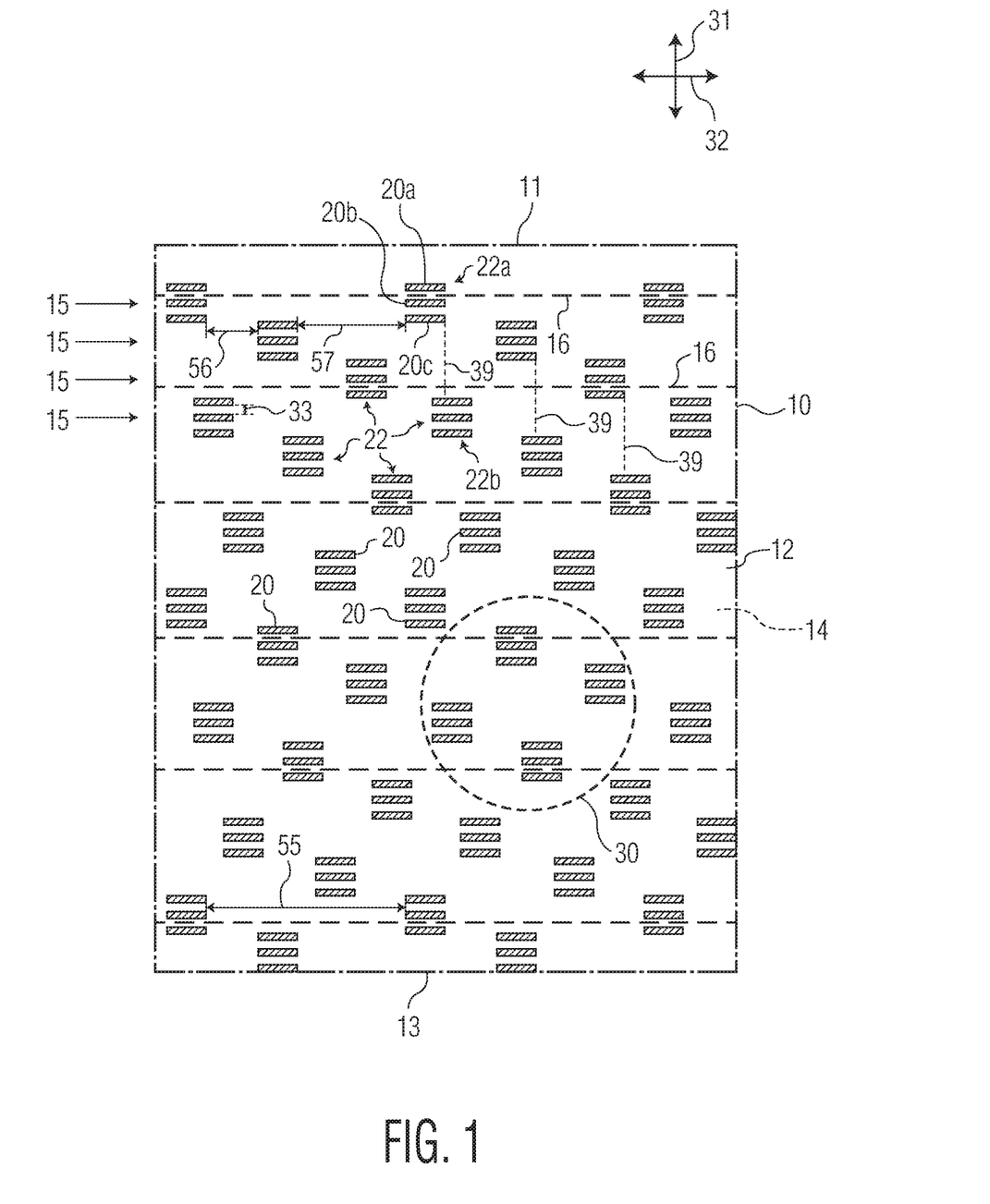
FIG. 1 is a plan view of an elasticated material according to aspects of the present disclosure.

FIG. 1 is a top plan view depicting a portion of exemplary elasticated material 10. The elasticated material 10 generally extends in both the longitudinal direction 31, between a top sheet edge 11 and a bottom sheet edge 13, and the lateral direction 32. The elasticated material 10 may generally comprise a first layer of material 12, a second layer of material 14, elastomeric strands 16, and bonds 20. As will be described in more detail below, at least some of the bonds 20 may be positioned on opposite sides of the elastomeric strands 16 in such a manner that the bonds 20 affix, or "entrap", portions of the elastomeric strands 16 in place within the elasticated material 10.

In general, the first layer of material 12 and the outer layer of material 14 may be constructed of any materials suitable for use in waistbands, leg cuffs, or any other body-contacting portions, or non-body-contacting portions, of clothing garments and absorbent articles. The layers 12, 14 may be constructed of the same material or different materials. Each of the layers 12, 14 may comprise a single layer, multiple layers, laminates, or the like in different contemplated embodiments. Additionally, the layers 12, 14 may comprise two separate webs of material positioned on opposite sides of the elastomeric strands 16 to form the elasticated material 10, or the layers 12, 14 may comprise a single web of material that is folded over such that a first portion of the web of material is positioned on a first side of the elastomeric strands 16 and a second portion of the web of material is positioned on a second side of the elastomeric strands 16 to form the elasticated material 10.

Exemplary suitable classes of materials for the layers 12, 14, include synthetic fibers (for example, polyethylene or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Additionally, various woven and non-woven fabrics can be used for the layers 12, 14. The layers 12, 14 can comprise woven fabrics, nonwoven fabrics, polymer films, film-fabric laminates or the like, as well as combinations thereof. Examples of nonwoven fabrics can include spunbond fabrics, meltblown fabrics, coform fabrics, carded webs, bonded-carded webs, bicomponent spunbond fabrics, spunlaces, or the like, as well as combinations thereof.

For example, the layers 12, 14 can be composed of a meltblown or spunbond webs of polyolefin fibers. Alternatively, the layers 12, 14 can be bonded-carded webs composed of natural and/or synthetic fibers. The layers 12, 14 can be composed of a substantially hydrophobic materials, and the hydrophobic materials can, optionally, be treated with a surfactant or otherwise processed to impart a desired level of wettability and hydrophilicity. The surfactant can be applied by any conventional means, such as spraying, printing, brush coating or the like. The surfactant can be applied to the entirety of the layers 12, 14 or it can be selectively applied to particular sections of the layers 12, 14. Some specific exemplary materials suitable for the layers 12, 14 include 100% polypropylene bonded-carded webs in the 5-150 gsm range. Other exemplary suitable materials include spunbond polypropylene non-woven webs in the 5-150 gsm range.

In an embodiment, the layers 12, 14 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, the layers 12, 14 can be spunbond substrates with a basis weight from about 8 to about 50 gsm. In an embodiment, the layers 12, 14 can be a 12 gsm spunbond-meltblown-spunbond substrate. In another embodiment, the layers 12, 14 can be an 8 gsm spunbond-meltblown-spunbond substrate.

Suitable elastomeric materials for the elastomeric strands 16 can include, but are not limited to, spandex elastomeric strands, strands of natural or synthetic rubber, thermoplastic elastomeric materials, or heat activated elastomeric materials. The elastomeric strands 16 can be any elastomeric material capable of being elongated at least about 50 percent, desirably about 350 percent, and capable of recovering to within at least about 250 percent, and desirably about 150 percent of its original length after being elongated about 300 percent. The elastomeric strands 16 can be a spandex elastomeric strand(s) such as, for example, a LYCRA thread commercially available from E. I. DuPont de Nemours and Co. Alternatively, the elastomeric strands 16 can be composed of a thermoplastic elastomer or a natural or a synthetic rubber commercially available from J.P.S. Elastomerics Corp. Alternatively, the elastomeric strands 16 can also be composed of a heat activated elastic material such as PEBAX, commercially available from Atochem, Inc., which can be activated with heat treatment after the elastomeric strands 16 have been disposed within the elasticated material 10 and the bonds 20 have been formed. In at least some embodiments, the elastomeric strands may have diameters that range between about 10 denier to about 1500 denier.

The bonds 20 are shown as bond groupings 22 with each bond grouping 22 comprising a plurality of bonds 20. In the embodiment of FIG. 1, each of the bond groupings 22 comprise three bonds 20, but the number could be different in other embodiments. For instance, the bond groupings 22 may otherwise comprise two bonds 20, four bonds 20, five bonds 20, six bonds 20, seven bonds 20, eight bonds 20, or any other suitable number of bonds 20. The bond groupings 22 may be defined by their relative longitudinal and lateral spacing. For example, bonds 20 located in close longitudinal and lateral proximity to each other may be part of the same bond grouping 22.

One exemplary bond grouping 22 is bond grouping 22a comprising bonds 20a, 20b, and 20c, with bond 20a being the longitudinally superior bond of the bond grouping 22a and the bond 20c being the longitudinally inferior bond of the bond grouping 22a. One feature of exemplary bond grouping 22a is the relative lateral spacing of the bonds 20a, 20b, and 20c with respect to each other. As can be seen, each of the bonds 20a, 20b, and 20c have the same lateral spacing within the material 10—that is, a center of each of the bonds 20a, 20b, and 20c are positioned at the same lateral position within the material 10. In the embodiment of FIG. 1, since each of the bonds 20a, 20b, and 20c have the same bond width 42, each of the bonds 20a, 20b, and 20c fully overlap each other in the longitudinal direction 31. However, in other embodiments, the bonds 20 of a bond grouping 22 may not have the exact same lateral spacing. Instead, there may be some lateral offset between longitudinally adjacent bonds 20 of bond groupings 22 such that the centers of the longitudinally adjacent bonds 20 do not align in the longitudinal direction 31. Although, the lateral offset may not be so great that there is no longitudinal overlap between the longitudinally adjacent bonds 20 of a bond grouping 22. Generally, the lateral offset between longitudinally adjacent bonds 20 of a bond grouping 22, such as bonds 20a and 20b of grouping 22a, may be such that a longitudinal overlap between the longitudinally adjacent bonds 20 is still greater than or equal to 10% of the bond width 42 of the longitudinally superior bond 20, which is bond 20a in the example of bond grouping 22a, or greater than or equal to 20%, greater than or equal to 30%, greater than or equal to 40%, greater than or equal to 50%, greater than or equal to 60%, greater than or equal to 70% of the of the bond width 42 of the longitudinally superior bond 20.

Another feature of bonds 20 which are part of the same bond grouping 22 is their longitudinal spacing 33. As can be seen in FIG. 1, the longitudinal spacing 33 between bonds 20a and 20b, and 20b and 20c, of bond grouping 22a is much less than a longitudinal spacing between bonds 20a and the next, closest longitudinally overlapping bond 20 above bond 20a, of which there is none, or the longitudinal spacing between bond 20c and the next, closest longitudinally overlapping bond, which comprises a bond of the bond grouping 22b. As can be seen the longitudinal spacing 33 between the longitudinally adjacent and overlapping bonds 20a and 20b, and between 20b and 20c, is much less than the distance between any other bonds 20 which are longitudinally adjacent and overlapping to bonds 20a, 20c. Accordingly, this combination of close longitudinal and lateral spacing is what defines a bond grouping 22.

The bond groupings 22 are further disposed in bond grouping rows 15, with bond groupings 22 within a bond row 15 having similar, although not necessarily exact longitudinal spacing. That is, bond groupings 22 within the same bond grouping row 15 may be positioned with no longitudinal offsets where the bond groupings 22 have the same longitudinal positioning, or small longitudinal offsets. Where the bond groupings 22 within the same bond grouping row 15 do have longitudinal offsets, the longitudinal offsets may be such that laterally adjacent bond groupings 22 within the same bond grouping row 15 still have a lateral overlap (e.g. the longitudinal extent the bond groupings 22 overlap in the lateral direction 32) that is greater than or equal to 10% of the bond grouping height 38 of the bond grouping 22 which is laterally prior to the laterally adjacent bond grouping 22, moving from left to right in FIG. 1, or greater than or equal to 20%, or greater than or equal to 30%, or greater than or equal to 40%, or greater than or equal to 50%, or greater than or equal to 60%, or greater than or equal to 70% of the bond grouping 22 which is laterally prior to the laterally adjacent bond grouping 22, moving from left to right in FIG. 1.

The bond groupings 22 within the same bond grouping row 15 may further have a lateral spacing 55 between laterally adjacent bond groupings 22 within the same row. In some embodiments, this lateral spacing 55 may be the same between all bond groupings 22 within the same row 15. However, in other embodiments, there may be some variations in the spacing 55 between laterally adjacent bond groupings 22 within the same bond grouping row 15. In some embodiments, the variation in lateral spacing 55 between bond groupings 22 within the same row 15 may be less than about 25% of the largest lateral spacing 55 between bond groupings 22 within the same row 15, or less than about 20%, or less than about 15%, or less than about 10%, or less than about 5% of the largest lateral spacing 55 between bond groupings 22 within the same row 15. As one illustrative example, where the largest spacing 55 between laterally adjacent bond groupings 22 within the same row 15 is 10 mm, the smallest spacing 55 may be less than about 7.5 mm, with the difference of 2.5 mm being 25% of the largest spacing 55.

Another feature of bond groupings 22 is the relation of the close longitudinal spacing 33 between bonds 20 within a bond grouping 22 to the diameter of the elastomeric strands of the material 10. More specifically, the distance 33 may generally be less than the un-tensioned diameter of the elastomeric strands 16 which traverse the material 10. Accordingly, where the elastomeric strands 16 pass between any bonds 20 of a single bond grouping 22, the bonds 20 disposed on either side of the elastomeric strand 16 may be "entrap" the elastomeric strand 16. To form the material 10 where the elastomeric strands 16 are entrapped along portions of their length between bonds 20 of bond groupings 22, the elasticated material 10 may be formed with the elastomeric strands 16 in a stretched state. As will be described in more detail below, this stretching of the elastomeric strands 16 decreases the diameter of the strands 16, allowing for passage through bond-forming portions of a patterned bond-forming apparatus when the strands 16 would have a diameter too large to pass between such bond-forming portions in their relaxed state.

When the elastomeric strands 16 are allowed to relax, they contract which also contracts the elasticated material 10. This contraction causes valleys where the bonds 20 are located and ridges between the bond groupings 22 to form within the elasticated material 10. The formed ridges may generally be oriented in a direction perpendicular to the axis 28 of the elastomeric strands 16, which in the embodiment of FIG. 1 is in the lateral direction 32. As can be seen in FIG. 1, the particular pattern shown does not allow for any continuously extending ridges to form in the material 10, which would correspond to continuously extending valleys.

A further feature of the bond pattern of the material 10 in FIG. 1 is the longitudinal overlapping of the bond groupings 22. In the example of FIG. 1, it can be seen that for a given bond grouping 22, none of the bond groupings 22 of the two bond grouping rows 15 longitudinally above and below the given bond grouping 22 longitudinally overlap the given bond grouping 22. However, for the given bond grouping 22, bond groupings 22 of the third bond grouping rows 15 longitudinally above and below the given bond grouping 22 longitudinally overlap the given bond grouping 22. This longitudinally overlapping relationship can be seen more clearly with respect to dotted lines 39. The dotted lines 39 are drawn longitudinally from an edge of a bond grouping 22 until contacting another bond grouping 22. As can be seen, each of the dotted lines 39 pass through two bond grouping rows 15 before contacting another bond grouping 22.

By staggering the lateral positioning of the bond groupings 22 of adjacent bond grouping rows 15 in such a manner, the material 10 forms ridges and valleys which are relatively non-continuous in a relaxed state. One benefit of these non-continuous valleys and ridges, is that the material 10 may present a barrier to fluid flow. As will be described in more detail below, the material 10 may be useful in a number of different locations within an absorbent article, which are generally constructed in an attempt to contain liquid insults within the article. When a liquid insult occurs, the liquid begins to spread within the absorbent article. Accordingly, the relatively non-continuous nature of the ridges and valleys formed by the material 10 helps to prevent the fluid from easily traversing the material 10 and potentially escaping containment.

It should be understood that different patterns than that disclosed in FIG. 1 may achieve a similar result with respect to forming relatively non-continuous valleys and ridges. For example, in other embodiments contemplated by the present disclosure, for a given bond grouping 22, none of the bond groupings 22 of only the closest bond grouping rows 22 longitudinally above and below the given bond grouping 22 may longitudinally overlap the given bond grouping 22. In such embodiments, for the given bond grouping 22, bond groupings 22 of the second bond grouping rows 15 longitudinally above and below the given bond grouping 22 may longitudinally overlap the given bond grouping 22 such that bond groupings 22 of every other row 15 longitudinally overlap. In still further contemplated embodiments, for a given bond grouping 22, there may be no longitudinal overlap between the given bond grouping 22 and bond groupings 22 of the closest three, four, or five rows 15 which are longitudinally above and below the given bond grouping 22. Extending this no overlapping concept to beyond five rows 15 on either side of a given bond grouping 22 may form ridges which are continuous for too great of a length, thereby limiting the ability of the material to be a barrier to fluid flow.

Figure 2:
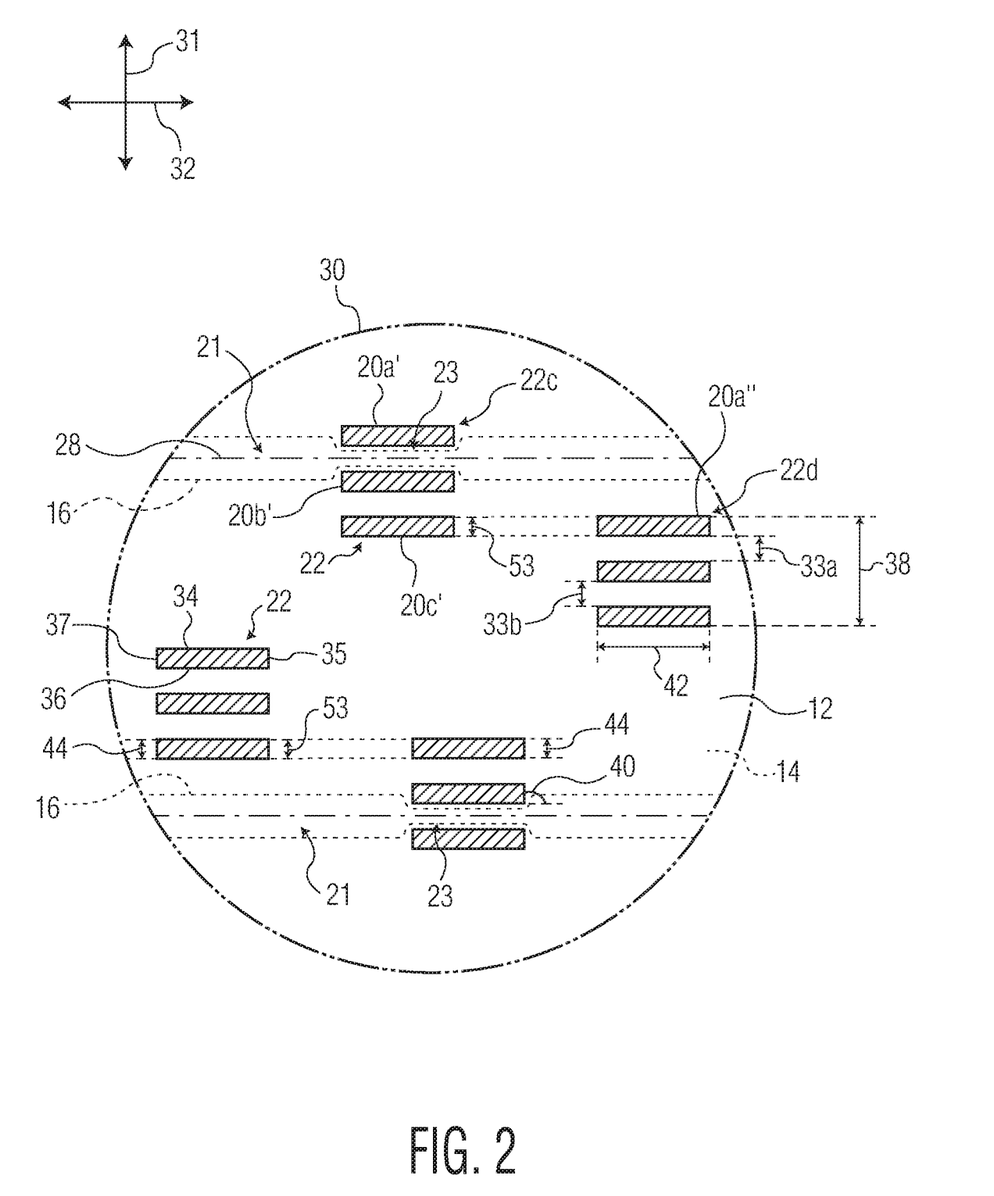
FIG. 2 close-up view of a portion of the elasticated material of FIG. 1.

FIG. 2 depicts a close-up view of circle 31 of FIG. 1, detailing the bonds 20 and elastomeric strands 16 of the elasticated material 10 in more detail. Specifically, FIG. 2 depicts with dashed lines the outer edges of the elastomeric strands 16 as they pass between bonds 20 of bond pairs 22, entrapping the strands 16. As can be seen, the elastomeric strands 16 in FIG. 2 may have non-entrapped portions 21 and entrapped portions 23.

In order to form a material such as the elasticated material 10, with elastomeric strands 16 comprising non-entrapped portions 21 and entrapped portions 23, the elastomeric strands 16 may be stretched before or as the elastomeric strands 16 are positioned between the first layer of material 12 and the second layer of material 14. The elastomeric strands 16 may have an un-tensioned outer diameter, and the outer diameter of the elastomeric strands 16 may decrease as the strands 16 are stretched. Accordingly, before or at the time the strands 16 are placed between the first layer of material 12 and the second layer of material 14, the elastomeric strands 16 may have an outer diameter that is less than the un-tensioned outer diameter of the elastomeric strands 16. Then, at least some of the bonds 20 of the material 10 may be placed on opposite sides of the stretched elastomeric strands 16 and spaced apart longitudinally across the elastomeric strands 16 a longitudinal distance 33.

The resulting structure of forming the elasticated material 10 in this manner can be seen with respect to the elastomeric strand 16 traversing through bond grouping 22c, which comprises bonds 20a', 20b', and 20c'. As the elastomeric strands 16 are allowed to relax, the outer diameter of the elastomeric strands 16 generally increases back toward their un-tensioned outer diameter. However, as can be seen in FIG. 2 within the context of bond grouping 22c, this expansion is inhibited in the entrapped portions 23 of the elastomeric strand 16 by the bonds 22a' and 22b' which are positioned across the strands 16 a longitudinal distance less than the un-tensioned diameter of the strands 16. Where the elastomeric strand 16 is not disposed between the bonds 22a' and 22b', the elastomeric strand 16 expands in the longitudinal direction (e.g. the outer diameter of the elastomeric strands 16 increases), resulting in the structure as seen in FIG. 2 with the elastomeric strand 16 shown having a larger outer diameter in the non-entrapped portions 21 than in the entrapped portions 23. In this manner, the portion of the strands 16 between the bonds 20 are "trapped" between the bonds 20 and the strands 16 are unable to slide in the lateral direction 32 between the bonds 20, thereby affixing the strands 16 to the material 10 at the location of the bonds 20.

It should be understood that the greater diameter of the elastomeric strands 16 in the non-entrapped portions 21 may be the same as the un-tensioned diameter of the strands 16, but in other embodiments this may not be the case. For example, the specific configuration of the type of elastomeric strand 16, the amount of elongation of the elastomeric strand 16 in the forming process, and the location of the bonds 20 of the bond groupings 22 in relation to the elongated elastomeric strand 16, both in the longitudinal spacing 22 of the bonds 20 that span the elastomeric strand 16 and in the lateral distance between bond groupings 22, may prevent the diameter of the elastomeric strands 16 from expanding in the non-entrapped portions 21 all the way back to its un-tensioned diameter. Accordingly, in some embodiments the expanded diameter in the non-entrapped portions 21 of at least some of the elastomeric strands 16 of the material 10 may still be less than the un-tensioned diameter of the elastomeric strands 16.

In order for the bonds 20 to entrap the elastomeric strands 16, the longitudinal spacing 33 between longitudinally adjacent bonds 20 of the same bond grouping 22, such as bonds 20a' and 20b' of bond grouping 22c, needs to be less than the un-tensioned diameter of the elastomeric strands 16. In some embodiments the spacing 33 between a first pair of the bonds 20 of a bond grouping 22, such as bonds 20a' and 20b', may be the same as the spacing 33 between a second pair of the bonds 20 of the bond grouping 20, such as bonds 20b' and 20c'. However, in other embodiments the spacings 33 may be different. For instance, the spacing 33a between a first pair of bonds 20 of bond grouping 22d may be different than the spacing 33b between a second pair of bonds 20 of the bond grouping 22d. However, in these embodiments, both of the spacings 33a, 33b may both be less than the un-tensioned diameter of the elastomeric strands 16.

Another feature of the bond pattern shown in FIGS. 1 and 2 is the lateral overlap of one or more individual bonds 20 of a first bond grouping 22 with one or more individual bonds 20 of a second bond grouping 22, with the first bond grouping 22 and the second bond grouping 22 located in adjacent bond grouping rows 15. Such a lateral overlap may be seen in more detail between the bond groupings 22a and 22d in FIG. 2. In the example of FIG. 2, the bond 20a" laterally overlaps with the bond grouping 22c for an overlap distance 53.

In some embodiments, the overlap distance 53 may be the same as the bond height 44. In such embodiments, the bonds 20c' and 20a" may be located at the same longitudinal position within the material 10 and fully overlap each other in the lateral direction 32. In other embodiments, however, the overlap distance 53 may be less than the bond height 44. In these embodiments, the bond grouping row 15 comprising the bond grouping 22d may be disposed further longitudinally below the bond grouping row 15 comprising the bond grouping 22c than the embodiments where the overlap distance 53 is the same as the bond height 44. Where the overlap distance is less than the bond height 44, the overlap distance 53 may be between about 0% and about 95% of the bond height 44, or between about 0% and about 80%, or between about 0% and about 65%, or between about 0% and about 50%, or between about 0% and about 35%, or between about 0% and about 20%, or between about 0% and about 5% of the bond height 44. In these embodiments, having a 0% overlap means that a top edge of the bond 20a" aligns with the bottom edge of the bond 20c'.

In further embodiments, the overlap distance 53 may be even greater than the bond height 44. In such embodiments, the overlap distance 53 may range between about 100% of the bond height 44 and value equal to the tow times the bond height 44 plus the longitudinal spacing 33. In the context of the embodiment of FIG. 2, at the top end of this range the bond 20a" would align laterally with the bond 20b'.

One benefit of a bond configuration where bonds 20 of different bond groupings 22 which are disposed in longitudinally adjacent rows 15 have some lateral overlap is that the elastomeric strands 16 may be positioned at any longitudinal position during manufacture and become entrapped within the material 10. For example, at any longitudinal position, other than directly in line with a bond 20, an elastomeric strand 16 will pass between bonds 20 within the same bond grouping 22, thereby becoming entrapped. Even where the elastomeric strands 16 are positioned directly in line with a bond 20 during manufacture, the elastomeric strands 16 are often pushed to one side of the bond-forming element of the pattern roll as the bond 20 is being formed, which would locate the elastomeric strand 16 between bonds 20 within the same bond grouping 22 and cause the strand 16 to become entrapped. In contrast, bond patterns with bonds 20 positioned only where the elastomeric strands 16 are desired to be located may require tightly controlling the longitudinal positioning of the elastomeric strands 16 during manufacture to ensure the strands 16 fall between bonds 20 and become entrapped. Tightly controlling the positioning of the elastomeric strands 16 can be difficult and may require expensive control equipment or may require manufacturing speeds which are less than desired. Additionally, such embodiments may require changing the pattern roll of a bonder to a pattern roll with a different bond pattern to produce different product sizes where the longitudinal positioning of the elastomeric strands 16 are different. Conversely, the bond patterns of the present disclosure allow for simply changing the longitudinal positioning of the elastomeric strands 16 to produce such different product sizes. Accordingly, the bond patterns of the present disclosure eliminate these drawbacks.

In still further embodiments of the present disclosure, there may be no lateral overlap between individual bonds 20 of bond groupings 22 which are in longitudinally adjacent rows 15. In the example of FIG. 2, this may mean that there is some amount of longitudinal separation between the bonds 20a" and 20c'. In these embodiments, this longitudinal separation may be limited to a distance equal to the bond height 44. Such embodiments may still exhibit the described benefits of the bond patterns of the present disclosure where the bonds 20 of different bond groupings 22 which are disposed in longitudinally adjacent rows 15 have some lateral overlap.

A further feature of the bond patterns of the present disclosure is the lateral offset between laterally adjacent bond groupings 22 of longitudinally adjacent bond grouping rows 15. For example, a single bond grouping 22 in a given bond grouping row 15 may be positioned between two bond groupings 22 of a row 15 which is disposed longitudinally above the given bond grouping row 15. However, the single bond grouping 22 may not be positioned equidistant between the two bond groupings 22. Instead, the single bond grouping 22 may be disposed a first lateral distance 56 from a first one of the two bond groupings 22 and a second lateral distance 57 from a second one of the two bond groupings 22. In some embodiments, the first lateral distance 56 may be between about 10% and about 40%, or between about 15% and about 30%, of the lateral spacing 55 between two bond groupings 22 within the same bond grouping row 15. The second lateral distance may be between about 50% and about 70%, or between about 50% and about 60%, of the lateral spacing 55 between two bond groupings 22 within the same bond grouping row 15. Such lateral spacing between bond groups 22 within adjacent bond grouping rows 15 helps to ensure that Bonds With respect to forming the bonds 20, the bonds 20 can be formed through any suitable bonding technique, such as thermal/heat bonding, ultrasonic bonding, pressure bonding, or other known bonding techniques. In general, as will be described in more detail below, the bonds 20 can be formed by use of a pattern component and a smooth component. To form the bonds 20, the layers 12, 14, with the elastomeric strands 16 disposed therebetween, are positioned between the pattern component and the smooth component with appropriate alignment between any bond-forming elements of the pattern component and the elastomeric strands 16. For instance, the elastomeric strands 16 may be positioned between bond-forming elements, such as raised protrusions, of the pattern component in order to form a material with entrapped elastomeric strands 16.

Where thermal bonding, pressure bonding, or rotary ultrasonic bonding techniques are used to form the bonds 20, the pattern component and the smooth component may be pattern rolls and smooth rolls, respectively. In such embodiments, the pattern rolls may contain a number of bond-forming elements, for example raised portions, that protrude from the surface of the pattern rolls. These bond-forming elements may correspond approximately with the shape of the bonds 20 and aligned on the surface of the pattern rolls to produce the longitudinal and lateral alignment of the bonds 20 as depicted in the different embodiments of the elasticated materials 10 of the present disclosure. The smooth rolls may generally be solid rolls with smooth outer surfaces.

The heat bonding techniques which may be used to form the bonds 20 may include heating the raised portions of the pattern rolls to between about 70 degrees C. and about 340 degrees C. In general, the level of heating should be less than that which results in melting of the elastomeric strands 16 when the bonds are being formed. While the bond-forming elements are at the appropriate temperature, the pattern roll may be pressed onto the smooth roll, with the layers 12, 14 and the elastomeric strands 16 positioned between the rolls. As some examples, the compressive force used to form the bonds 20 may be between about 500 KPa and about 2,750 KPa, and the layers 12, 14 and the elastomeric strands 16 may pass between the pattern and anvil rolls between about 100 linear meters per minute (mpm) and about 350 (mpm).

The rotary ultrasonic bonding techniques that may be used to form the bonds 20 may use ultrasonic energy in order to form the bonds 20. For instance, as the layers 12, 14 and the elastomeric strands 16 pass between the pattern roll and smooth roll of a rotary ultrasonic bonder, the smooth roll may be vibrated at a frequency of between about 20,000 Hz and about 50,000 Hz, causing internal heating of the layers 12, 14 to such an extent that the layers 12, 14 melt together forming the bonds 20.

The pressure bonding techniques which may be used to form the bonds 20 may be similar to the heat bonding techniques described above, except that no external heat may need to be applied to the bond-forming elements of the pattern roll. However, in order to compensate for the bond-forming elements only being at an ambient temperature, the compressive force applied to the pattern roll and the smooth roll to form the bonds 20 must be greatly increased. In some examples, a compressive force is applied to produce a nip force of between about 0.1 KN and about 5 KN, while the layers 12, 14 and the elastomeric strands 16 pass between the pattern roll and the anvil roll at about 15 mpm and 450 mpm.

In non-rotary ultrasonic bonding techniques that may be used to form the bonds 20, the pattern element and the anvil element may be a smooth ultrasonic horn and a patterned anvil. In such embodiments, the anvil component may have the bond-forming elements, while the ultrasonic horn has a generally smooth surface. Like with the rotary ultrasonic techniques, the ultrasonic horn may be vibrated at a frequency of between about 20,000 Hz and about 50,000 Hz, as the layers 12, 14 and the elastomeric strands 16 pass between the ultrasonic horn and the patterned anvil. This ultrasonic energy application causes internal heating of the layers 12, 14 to such an extent that the layers 12, 14 melt together forming the bonds 20.

In general, such heat bonding techniques, ultrasonic bonding techniques, and pressure bonding techniques known in the art. It should be understood that the parameters described for the different techniques are only exemplary suitable parameters. The described techniques may be used to form the bonds 20 using such techniques operating with other suitable parameters, as is known in the art. For instance, PCT Patent Application WO 2010/068150, titled "METHOD AND APPARATUS FOR BONDING", which is incorporated herein by reference in its entirety, details methods and apparatus for performing pressure bonding which could be used to form the bonds 20 of the bond patterns described in the present disclosure using many different suitable parameters. It should additionally be understood that the different ways in which the bonds 20 are formed do not appreciably affect the resulting structure of the elasticated material, aside from possibly resulting in different strengths of bonds. However, all of such known techniques are capable of producing bonds which are strong enough to resist the expansion in diameter of the elastomeric strands positioned between the bonds without breaking. Accordingly, the bonds 20 may be formed according to any known bonding technique without departing from the scope of the present disclosure.

In general, the bonds 20 of the elasticated materials of the present disclosure may have any suitable size or shape. However, in at least some embodiments, the bonds may range between about 50 square micrometers to about 20 square millimeters, or between about 70 square micrometers to about 10 square millimeters, or between about 250 square micrometers and about 5 square millimeters. Additionally, in some embodiments, the dimension of the bonds 20 in a direction generally parallel to the elastomeric strands 16 may be between about two times to about six times greater than the dimension of the bonds 20 that is generally perpendicular to or extending away from the elastomeric strands 16. For instance, in the embodiment of FIG. 2, the bond width 42 may be between about two times and about six times greater than the bond height 44.

FIG. 2 details additional features of bonds 20. For instance, bonds 20 may each include a top portion 34, a bottom portion 36 opposite the top portion 34, a first side portion 35, and a second side portion 37 opposite the first side portion 35. The side portions 35 and 37 may further form an angle with respect to the lateral axes 28 of the elastomeric strands 16, with the side portion 35 shown forming an angle 40 with respect to the axes 28. Although shown with angle 40 at 90 degrees relative to the elastomeric strands 16 in FIG. 2, in at least some embodiments the first side portions 35 of the bonds 20 may have an angle 40 which is other than 90 degrees. In some embodiments, the angle 40 may form an acute angle with respect to the lateral axis 28 of the elastomeric strand 16. In general, the angle 40 may range between about 15 degrees and about 90 degrees, or between about 30 degrees and about 89 degrees, or between about 50 degrees and about 88 degrees. In other embodiments, the angle 40 may range between about 105 degrees and about 180 degrees, or between about 120 degrees and about 179 degrees, or between about 140 degrees and about 178 degrees. The angle the opposing side portions 37 may form with the axes 28 may be complementary to the angle 40 formed by the side portion 35.

Where the bonds 20 have side portions 35 which form an angle 40 that is other than 90 degrees, the bonds 20 within a bond grouping 22 may be offset laterally an amount such that the side portions 35 of longitudinally adjacent bonds 20 align along a line that forms the angle 40 with respect to the axes 28. In some further embodiments, the bond groupings 22 of longitudinally adjacent bond grouping rows 15 may additionally be offset laterally such that the side portions 35 of the bonds 20 of a bond grouping 22 of a first row 15 and the bonds 20 of a second bond grouping 22 of a second row 15, where the second row 15 is longitudinally adjacent to the first row 15, align along a line that forms the angle 40 with respect to the axes 28.

Although shown as generally rectangular in FIG. 2, the bonds 20 may be any suitable shape. For instance, the bonds 20 may be circular, semi-circular, oval shaped, half-oval shaped, triangular, square, rectangular, trapezoidal, rhombus-shaped, parallelogram-shaped, or the like. In some embodiments, the bonds 20 can have three sides, four sides, five sides, six sides, or any other suitable number of sides.

As described previously, the material 10 of the present disclosure may be useful for a number of reasons, including preventing liquid from travelling through the material 10. Such a material 10 may particularly useful in absorbent articles and/or clothing garments. For instance, a primary function of absorbent articles is to absorb and contain bodily exudates that are discharged into the article. Use of, and strategically locating, materials such as material 10 may aid in preventing leakage of those bodily exudates. The particular bond patterns of the present disclosure may be useful for other reasons.

Figure 3:
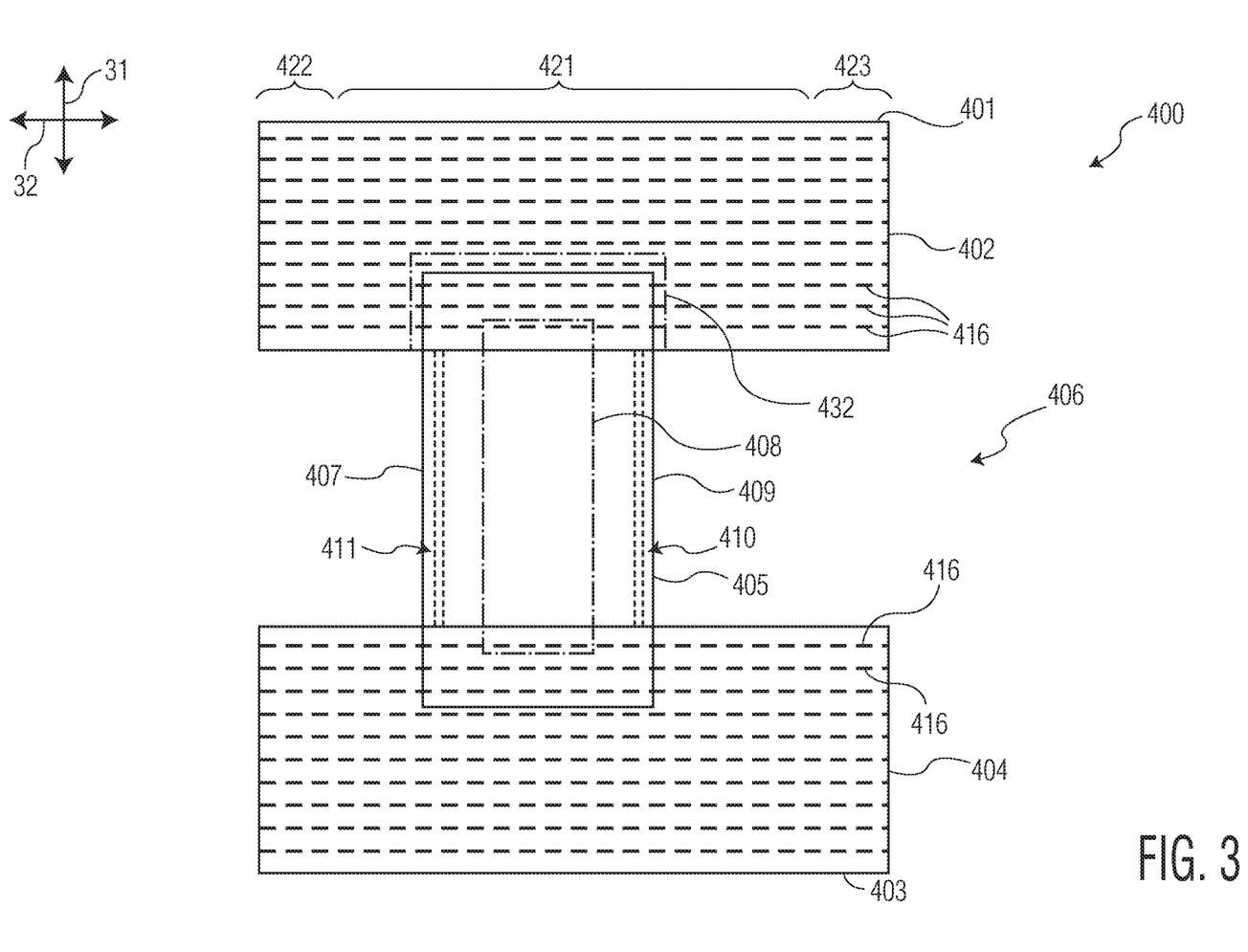
FIG. 3 is a plan view of an exemplary absorbent article including elasticated materials according to aspects of the present disclosure.

FIG. 3 illustrates exemplary absorbent article 400 which comprises an absorbent article manufactured in what is commonly termed a cross-machine direction (CD) process. However, it should be understood that other absorbent articles which are manufactured in machine-direction (MD) processes may contain elasticated materials according to the present disclosure without departing from the spirit and scope of the disclosure.

The absorbent article 400 can comprise a three-piece construction where the absorbent article 400 has a chassis 406 including a front waist panel 402 having a front waist edge 401, a rear waist panel 404 having a rear waist edge 403, and an absorbent panel 409 extending between the front waist panel 402 and the rear waist panel 404. The absorbent panel 409 may generally include absorbent body 408, which may be sandwiched between a garment-facing outer layer and a body-side facing layer, sometimes called a liner. In some embodiments, the absorbent panel 409 can have a first lateral side edge 405 and a second lateral side edge 407 and can overlap the front waist panel 402 and the rear waist panel 404. The absorbent panel 409 can be bonded to the front waist panel 402 and the rear waist panel 404 to define a three-piece construction. However, it is contemplated that an absorbent article can be manufactured in a CD process without being a three-piece construction garment, which is also sometimes referred to as a one-piece construction (not shown), as the front waist panel 402 and the rear waist panel 404 are integral with one another by way of commonly connected components forming the waist panel such as a bodyside liner and/or an outer cover which can envelope the absorbent panel 409 or simply cover the garment side of the absorbent panel 409.

The front waist panel 402 and the rear waist panel 404 may generally comprise elastomeric strands 416 disposed between at least two layers of material. For instance, the front waist panel 402 and the rear waist panel 404 may comprise an elasticated material as described herein, such as elasticated material 10. In at least some embodiments, the front waist panel 402 and/or the rear waist panel 404 may have a central region 421, and side edge regions 422, 423.

In some embodiments, the absorbent article 400 may include elasticated materials such as material 10 in order to help contain bodily exudates discharged within article 400. For instance, at least a portion of the front waist panel 402 may comprise the material 10. In some embodiments, the front waist panel 402 may comprise the material 10 within the central region 421. The side edge regions 422, 423, in different embodiments, may comprise a different elasticated material or may comprise the same material 10. In some further embodiments, only a portion of the front waist panel 402 proximate the absorbent panel 409 may comprise the material 10, such as the portion defined by box 432. In these embodiments, having the front waist panel 402, or portions of the front waist panel 402, comprise the material 10, the front waist panel 402 may present a barrier to fluid flow, thereby helping to reduce leakage of liquids out of the article 400.

In further embodiments, the material 10 may be used for other portions of the absorbent article 400. For example, the leg cuffs 410, 411 may also or additionally be comprised of the material 10 to further help reduce liquid leakage out of the article 400. In additional or alternative embodiments, barrier cuffs (not shown) may be comprised of the material 10 for the same reason.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

What is claimed is:

1. An absorbent article including front region, a crotch region, and a rear region, the article having a first side edge and a second side edge and further comprising:
   a first elasticated waist panel disposed in the front region;
   a second elasticated waist panel disposed in the rear region and spaced from the first elasticated waist panel; and
   an absorbent panel comprising an outer cover, a liner, and an absorbent body disposed between the outer cover and the liner, the absorbent panel spanning between and connecting the first elasticated waist panel and the second elasticated waist panel,
   wherein one of the first elasticated waist panel and the second elasticated waist panel comprises:
     a first layer of material;
     a second layer of material; and
     an elastomeric strand extending in a lateral direction in a straight manner through the first elasticated waist panel or the second elasticated waist panel and disposed between the first layer of material and the second layer of material;
   wherein the first layer of material and the second layer of material are bonded together by a plurality of bonds, the elastomeric strand being un-bonded to the first layer of material or the second layer of material by the plurality of bonds, the plurality of bonds being arranged in bond groupings aligned in bond grouping rows, each bond grouping comprising a plurality of bonds with each bond of the plurality of bonds spaced from adjacent bonds of a bond grouping a distance less than an un-tensioned diameter of the elastomeric strand, and with the elastomeric strand extending completely between a portion of a first bond facing the elastomeric strand and a portion of a second bond facing the elastomeric strand, the first bond and the second bond being part of a first bond grouping,
   wherein the first bond grouping is spaced from bond groupings longitudinally above and below the first bond grouping a longitudinal distance greater than the un-tensioned diameter of the elastomeric strand, and
   wherein a portion of a longitudinal extent of a second bond grouping overlaps a portion of a longitudinal extent of the first bond grouping in the lateral direction, the second bond grouping disposed in a bond grouping row longitudinally adjacent to the bond grouping row containing the first bond grouping.

2. The absorbent article of claim 1, wherein the elastomeric strand overlaps the absorbent body.

3. The absorbent article of claim 1, wherein the other one of the first elasticated waist panel and the second elasticated waist panel comprises:
a first layer of material;
a second layer of material; and
an elastomeric strand extending in a lateral direction in a straight manner through the other of the first elasticated waist panel and the second elasticated waist panel and disposed between the first layer of material and the second layer of material;
wherein the first layer of material and the second layer of material of the other of the first elasticated waist panel and the second elasticated waist panel are bonded together by a plurality of bonds, arranged in bond groupings aligned in bond grouping rows, each bond grouping comprising a plurality of bonds with each bond of the plurality of bonds spaced from adjacent bonds of a bond grouping a distance less than an un-tensioned diameter of the elastomeric strand with the elastomeric strand extending completely between a portion of a first bond facing the elastomeric strand and a portion of a second bond facing the elastomeric strand, the first bond and the second bond being part of a first bond grouping,
wherein the first bond grouping is spaced from bond groupings longitudinally above and below the first bond grouping a longitudinal distance greater than the un-tensioned diameter of the elastomeric strand, and
wherein a portion of a longitudinal extent of a second bond grouping overlaps a portion of a longitudinal extent of the first bond grouping in the lateral direction, the second bond grouping disposed in a bond grouping row longitudinally adjacent to the bond grouping row containing the first bond grouping.

4. The absorbent article of claim 1, wherein each of the first bond grouping and the second bond grouping comprises a longitudinally superior bond and a longitudinally inferior bond, and wherein a longitudinal extent of the longitudinally inferior bond of the first bond grouping overlaps a longitudinal extent of the longitudinally superior bond of the second bond grouping in the lateral direction.

5. The absorbent article of claim 4, wherein the overlap between the longitudinally inferior bond of the first bond grouping and the longitudinally superior bond of the second bond grouping comprises an overlap distance that is between 0% and 250% of a longitudinal height of the longitudinally inferior bond of the first bond grouping.

6. The absorbent article of claim 4, wherein the overlap between the longitudinally inferior bond of the first bond grouping and the longitudinally superior bond of the second bond grouping comprises an overlap distance that is between 0% and 100% of a longitudinal height of the longitudinally inferior bond of the first bond grouping.

7. The absorbent article of claim 1, wherein the first bond grouping and the second bond grouping each are formed of two bonds.

8. The absorbent article of claim 1, wherein the first bond grouping and the second bond grouping each are formed of three bonds.

9. The absorbent article of claim 1, wherein the first waist panel comprises a plurality of elastomeric strands, each of the plurality of elastomeric strands extending through bonds of different bond groupings, the bonds of the different bond groupings spaced apart longitudinally a distance less than an un-tensioned diameter of the elastomeric strand passing therethrough.

10. The absorbent article of claim 1, wherein the bond groups of the second bond group row are disposed unequal lateral distances from laterally adjacent bond groups of the first bond group row.

11. The absorbent article of claim 1, wherein the bond groupings of the second bond grouping row are disposed such that lateral extents of none of the bond groupings of the second bond grouping row overlap with lateral extents of the bond groupings of the first bond grouping row in the longitudinal direction.

12. The absorbent article of claim 11, further comprising a third bond grouping row disposed longitudinally adjacent to the second bond grouping row, with the second bond grouping row disposed longitudinally between the first bond grouping row and the third bond grouping row, wherein the bond groups of the third bond grouping row are disposed such that lateral extents of none of the bond groupings of the third bond grouping row overlap with lateral extents of the bond groupings of the first bond grouping row in the longitudinal direction.

13. The absorbent article of claim 12, further comprising a fourth bond grouping row disposed longitudinally adjacent to the third bond grouping row, with the third bond grouping row disposed longitudinally between the second bond grouping row and the fourth bond grouping row, wherein the bond groups of the fourth bond grouping row are disposed such that lateral extents of at least some of the bond groupings of the fourth bond grouping row overlap with lateral extents of the bond groupings of the first bond grouping row in the longitudinal direction.

* * * * *